United States Patent [19]

Ide et al.

[11] Patent Number: 5,696,306
[45] Date of Patent: Dec. 9, 1997

[54] DECOMPOSITION INHIBITOR FOR HYDROGEN- AND FLUORINE-CONTAINING HALOGENATED HYDROCARBONS AND METHOD OF INHIBITING DECOMPOSITION USING SAME

[75] Inventors: Satoshi Ide; Tatsumi Tsuchiya; Naoki Maekawa; Tsuyoshi Inaba; Hirokazu Aoyama, all of Settsu, Japan

[73] Assignee: Daikin Industries, Ltd., Osaka, Japan

[21] Appl. No.: 433,347

[22] PCT Filed: Nov. 10, 1993

[86] PCT No.: PCT/JP93/01639

§ 371 Date: Jun. 22, 1995

§ 102(e) Date: Jun. 22, 1995

[87] PCT Pub. No.: WO94/11329

PCT Pub. Date: May 26, 1994

[30] Foreign Application Priority Data

Nov. 10, 1992 [JP] Japan ..................... 4-300097
Apr. 19, 1993 [JP] Japan ..................... 5-91380

[51] Int. Cl.$^6$ ..................... C07C 19/08
[52] U.S. Cl. ..................... 570/109; 570/110; 570/111; 570/112; 570/117; 570/121
[58] Field of Search ..................... 570/109, 110, 570/111, 112, 117, 121

[56] References Cited

U.S. PATENT DOCUMENTS 4,960,535 10/1990 Logsdon et al. ..................... 252/171

OTHER PUBLICATIONS

The Merck Index, 8th ed. (1968) p. 683.

*Primary Examiner*—C. Warren Ivy
*Assistant Examiner*—Lyman Smith
*Attorney, Agent, or Firm*—Larson & Taylor

[57] ABSTRACT

A decomposition inhibitor for hydrochlorofluorocarbons and hydrofluorocarbons (HCFCs/HFCs) which comprises at least one member of the class consisting of organic acid-amine mixtures, fluorine-free halogenated hydrocarbons, carboxylic acid esters, nitrile compounds, carbonyl compounds and halogenated nitro compounds. A method of inhibiting the decomposition of HCFCs/HFCs which comprises using the decomposition inhibitor mentioned above.

In the field of polyurethane foam manufacture using HCFCs/HFCs as blowing agents, the effect of inhibiting the decomposition of HCFCs/HFCs can be produced over a long period of time covering the storage of raw materials, the foam manufacturing process and the use of foamed products.

6 Claims, No Drawings

DECOMPOSITION INHIBITOR FOR HYDROGEN- AND FLUORINE-CONTAINING HALOGENATED HYDROCARBONS AND METHOD OF INHIBITING DECOMPOSITION USING SAME

This application is a 35 USC 371 National Stage filing of PCT/JP93/01639 published as WO94/11329 on May 26,1994.

TECHNICAL FIELD

The present invention relates to a decomposition inhibitor for hydrogen- and fluorine-containing halogenated hydrocarbons and a method of inhibiting decomposition using the same. More particularly, the invention relates to a decomposition inhibitor capable of preventing hydrogen- and fluorine-containing halogenated hydrocarbons which are useful as blowing agents for foamed insulation materials (polyurethane foams) from decomposing during storage as raw materials for foamed insulation materials, during use as blowing agents (in the process of manufacturing foamed insulation materials) or during existence in the bubbles in products (foamed insulation materials) and relates to a method of using the same (for preventing hydrogen- and fluorine-containing halogenated hydrocarbons from decomposing).

In the present specification, "%" and "part(s)" mean "% by weight" and "part(s) by weight", respectively.

BACKGROUND ART

Polyurethane foams, which are produced by using organic polyisocyanates and polyols as principal raw materials, are known as typical foamed insulation materials.

Various blowing agents comprising "halogenated hydrocarbons with all the hydrogen atoms replaced by fluorine and chlorine" (hereinafter referred to as CFCs) have been proposed for use in the production of said polyurethane foams (cf. e.g. Japanese Kokai Tokkyo Koho JP 52-46005) and have been widely used on a large commercial scale.

However, CFCs contained in such blowing agents are known to destroy the ozone layer and therefore restrictions have been imposed on the production and use thereof.

Thus, the advent of novel blowing agents comparable in performance characteristics to CFCs and capable of serving as substitutes therefor has been awaited. For the time being, "hydrogen- and fluorine-containing halogenated hydrocarbons" (hereinafter referred to as HCFCs/HFCs) are regarded as promising since they involve no or little risk of depleting the ozone layer.

Regrettably, however, HCFCs/HFCs are generally lacking in stability as compared with the conventional CFCs. It is known that they are particularly unstable when used in the form of a mixture with an alcoholic hydroxyl-containing compound. In addition, they are readily decomposable in the presence of water an alkali or a metal or under the action of light or heat, for instance. Methods have been proposed for preventing the decomposition of HCFCs/HFCs, for example by adding a nitro-containing hydrocarbon (Japanese Kokai Tokkyo Koho JP 01-128944) or adding a nitro-containing hydrocarbon and an epoxide (Japanese Kokai Tokkyo Koho JP 01-128945).

The methods described in the above-cited patent specifications all aim to prevent the decomposition of such HCFCs/HFCs as mentioned above in an unstable state, for example in the presence of a polyol used as a raw material in the production of polyurethane foams.

However, the known methods described in the above laid-open patent specifications cannot be said to be fully satisfactory in the effect of inhibiting the decomposition of HCFCs/HFCs. This is because HCFCs/HFCs gradually decompose not only during storage thereof but also in the process of polyurethane foam manufacture using HCFCs/HFCs and during a long period of use of polyurethane foam products manufactured by using HCFCs/HFCs (said HCFCs/HFCs thus occurring in the foam (bubbles)). Accordingly, there has been earnestly desired the advent of a novel method of preventing the decomposition of HCFCs/HFCs and thus keeping the HCFCs/HFCs stable under any of the condition mentioned above.

DISCLOSURE OF THE INVENTION

In view of the state of the art as mentioned above, the present inventors made intensive research and found the following:

[A] (1) Mixtures of an organic acid and an amine, in particular mixtures of a carboxylic acid having an acid dissociation constant (pKa) of not more than 5 and a tertiary amine having an acid dissociation constant (pKa) of not more than 10;

(2) fluorine-free halogenated hydrocarbons, in particular specific chlorinated hydrocarbons;

(3) carboxylic acid esters, in particular condensates from a carboxylic acid having an acid dissociation constant (pKa) of not more than 5 and an alcohol containing 1 to 5 carbon atoms;

(4) nitrile compounds, in particular nitrile compounds of the formula $R^1$—CN wherein $R^1$ is an alkyl group containing 1 to 5 carbon atoms or a haloalkyl group containing 1 to 5 carbons;

(5) carbonyl compounds, in particular carbonyl compounds of the formula

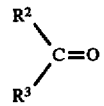

wherein $R^2$ and $R^3$ are the same or different and each is an alkyl group containing 1 to 3 carbon atoms or a haloalkyl group containing 1 to 3 carbon atoms; and (6) halogenated nitro compounds, in particular halogenated nitro compounds of the formula $R^4$—$NO_2$ wherein $R^4$ is a $C_{1-5}$ alkyl group substituted by at least one halogen atom or a phenyl group substituted by at least one halogen atom have excellent performance characteristics as decomposition inhibitors for HCFCs/HFCs, in particular for 1,1-dichloro-2,2,2-trifluoroethane, 1,1-dichloro-1-fluoroethane, 1,1,2,2,3-pentafluoropropane, 1,1,1,4,4,4-hexafluorobutane, 1,1,2,2,3,3,4,4-octafluorobutane and 1,1,1,2-tetrafluoroethane;

[B] When used in combination with an aliphatic or aromatic nitro compound, the above-mentioned compounds (1) to (6) are improved in the effect of preventing the decomposition of hydrogen- and fluorine-containing halogenated hydrocarbons (HCFCs/HFCs);

[C] Furthermore, when these compounds are used as decomposition inhibitors, the decomposition inhibiting effect can be attained for a long period of time with HCFCs/HFCs in any circumstance, irrespective of the presence or absence of a polyol (i.e. an alcoholic hydroxyl-containing compound), namely in the presence of a polyol premixed therewith to give a raw material preparation for polyurethane foam manufacture (during storage), during the use as blowing agents in the production of polyurethane foams (in the step of foam manufacture) or during the occurrence in the bubbles in the polyurethane foam products (during use).

Thus, the present invention provides a decomposition inhibitor for hydrogen- and fluorine-containing halogenated hydrocarbons which comprises at least one member of the class consisting of organic acid-amine mixtures, fluorine-free halogenated hydrocarbons, carboxylic acid esters, nitrile compounds, carbonyl compounds and halogenated nitro compounds.

The invention also provides a method of inhibiting the decomposition of hydrogen- and fluorine-containing halogenated hydrocarbons which comprises using a decomposition inhibitor comprising at least one member of the class consisting of organic acid-amine mixtures, fluorine-free halogenated hydrocarbons, carboxylic acid esters, nitrile compounds, carbonyl compounds and halogenated nitro compounds.

In the organic acid-amine mixtures to serve as decomposition inhibitors for HCFCs/HFCs in accordance with the present invention, the organic acid is preferably a carboxylic acid having an acid dissociation constant (pKa) of not more than 5, for example a halogenated carboxylic acid such as monochloroacetic acid, dichloroacetic acid, trichloroacetic acid, trifluoroacetic acid or chlorobenzoic acid, aminobenzoic acid, nitrobenzoic acid, formic acid, citric acid, glutamic acid, oxalic acid, etc.

The amine is preferably a tertiary amine having an acid dissociation constant (pKa) of not more than 10, for example triethylenediamine, methylmorpholine, dimethylimidazole, dimethylaniline, methylpyrrole, pyridine, aminopyridine, methylpyridine, quinoline, etc.

The organic acid and amine to be combinedly used and the proportions thereof can be arbitrarily selected according to the target HCFC or HFC, the other substances to be admixed therewith, the temperature conditions during storage, use (product manufacture) and use of foamed products, and other factors. Generally, however, preferable examples of the combination of an organic acid with an amine include combinations of monochloroacetic acid with dimethylimidazole, dimethylaniline or methylpyrrole. The combinations which are soluble in the HCFC/HFC are preferred. When such an organic acid-amine mixture is used singly as the decomposition inhibitor, said mixture is used generally in a proportion of 0.1 to 20%, preferably in a proportion of 1 to 10%, relative to the blowing agent.

The fluorine-free halogenated hydrocarbons to serve as decomposition inhibitors for HCFCs/HFCs in accordance with the invention are, for example, 1,1-dichloroethane, 1,1,1-trichloroethane, 1,1,1,2-tetrachloroethane, 1,1,2,2-tetrachloroethane, 1-chloropropane, 2-chloropropane, 1-chloro-2-methylpropane, 2-chloro-2-methylpropane, 1-chlorobutane, 2-chlorobutane, bromoethane, isopropyl bromide, n-propyl bromide, iodoethane, etc. Preferred among them are 1,1,1,2-tetrachloroethane, 2-chloro-2-methylpropane, 1-chloropropane and 2-chloropropane.

When such a fluorine-free halogenated hydrocarbon is used singly as the decomposition inhibitor, the amount thereof can be arbitrarily selected according to the other substances to be mixed therewith, the temperature conditions during storage, use (product manufacture), and use of foamed products, and other factors. Generally, it is used in a proportion of 1 to 50%, preferably 5 to 30%, relative to the blowing agent.

The carboxylic acid esters to serve as decomposition inhibitors for HCFCs/HFCs in accordance with the present invention are preferably condensates of a carboxylic acid having an acid dissociation constant (pKa) of not more than 5 and an alcohol containing 1 to 5 carbon atoms, for example methyl chloroacetate, ethyl chloroacetate, propyl chloroacetate, isopropyl chloroacetate, methyl bromoacetate, ethyl bromoacetate, propyl bromoacetate, methyl fluoroacetate, ethyl fluoroacetate, propyl fluoroacetate, methyl acetate, ethyl acetate, propyl acetate, ethyl acrylate, vinyl acrylate, vinyl methacrylate, methyl acetate, methyl salicylate, etc. More preferred among these are methyl chloroacetate, ethyl chloroacetate, isopropyl chloroacetate, methyl bromoacetate, ethyl bromoacetate, etc.

When such a carboxylic acid ester is used singly as the decomposition inhibitor, its amount can be arbitrarily selected according to the other substances to be mixed therewith, the temperature conditions during storage, use (product manufacture), and use of foamed products, and other factors, generally in an amount of 0.1 to 20%, preferably 1 to 10%, relative to the blowing agent.

The nitrile compounds to serve as decomposition inhibitors in accordance with the present invention are preferably represented by the formula $R^1$—CN wherein $R^1$ is an alkyl group containing 1 to 5 carbon atoms or a haloalkyl group containing 1 to 5 carbon atoms, and include, among others, acetonitrile, propionitrile, butyronitrile, valeronitrile, hexanonitrile, monochloroacetonitrile, dichloroacetonitrile, trichloroacetonitrile, α-chloropropionitrile, β-chloropropionitrile, monobromoacetonitrile, α-bromopropionitrile and β-bromopropionitrile. More preferred among these are those soluble in HCFCs/HFCs, such as monochloroacetonitrile, dichloroacetonitrile, trichloroacetonitrile, α-chloropropionitrile, β-chloropropionitrile, monobromoacetonitrile, α-bromopropionitrile, β-bromopropionitrile, etc.

When such a nitrile compound is used singly as the decomposition inhibitor, it is used in an amount that can be arbitrarily selected according to the target HCFC or HFC, the other substances to be admixed therewith, the temperature conditions of storage, use, and use of foamed products, and other factors, generally in a proportion of 0.1 to 20%, preferably 1 to 10%, relative to HCFCs/HFCs.

The carbonyl compounds to serve as decomposition inhibitors in accordance with the present invention are preferably represented by the formula

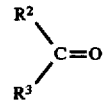

wherein $R^2$ and $R^3$ are the same or different and each is an alkyl group containing 1 to 3 carbon atoms or a haloalkyl group containing 1 to 3 carbon atoms, and include, among others, acetone, 2-butanone, 2-pentanone, 3-pentanone, 1-chloroacetone, 1,3-dichloroacetone, 1,1-dichloroacetone, 1-bromoacetone, 1,3-dibromoacetone and 1,1-dibromoacetone. More preferred among these are those soluble in HCFCs/HFCs, such as 1-chloroacetone, 1,3-dichloroacetone, 1,1-dichloroacetone, 1-bromoacetone, 1,3-dibromoacetone, 1,1-dibromoacetone, etc.

When such a carbonyl compound is used singly as the decomposition inhibitor, it is used in an amount that can be arbitrarily selected according to the target HCFC or HFC the other substances to be admixed therewith, the temperature conditions of storage, use, and use of foamed products, and other factors, generally in a proportion of 0.1 to 20%, preferably 1 to 10%, relative to HCFCs/HFCs.

The halogenated nitro compounds to serve as decomposition inhibitors in accordance with the present invention are preferably represented by the formula $R^4$—$NO_2$ wherein $R^4$ is a $C_{1-5}$ alkyl group substituted by at least one halogen atom or a phenyl group substituted by at least one halogen atom, and include, among others, monochloronitromethane, α-chloronitroethane, β-chloronitroethane, o-chloronitrobenzene, m-chloronitrobenzene, p-chloronitrobenzene, o-chloronitrotoluene, m-chloronitrotoluene, p-chloronitrotoluene, monobromonitromethane, α-bromonitroethane, β-bromonitroethane, o-bromonitrobenzene, m-bromonitrobenzene, p-bromonitrobenzene, o-bromonitrotoluene, m-bromonitrotoluene and p-bromonitrotoluene. More preferred among these are monochloronitromethane, α-chloronitroethane, β-chloronitroethane, monobromonitromethane, α-bromonitroethane and β-bromonitroethane.

When such a halogenated nitro compound is used singly as the decomposition inhibitor, it is used in an amount that can be arbitrarily selected according to the target HCFC or HFC the other substances to be admixed therewith, the temperature conditions of storage, use, and use of foamed products, and other factors, generally in an amount of 0.1 to 20%, preferably 1 to 20%, relative to HCFCs/HFCs.

In practicing the decomposition inhibiting method of the invention, any of the known conventional decomposition inhibitors can be used combinedly with the above-mentioned specific decomposition inhibitors characterizing the present invention, to stabilize HCFCs/HFCs against decomposition.

As such known decomposition inhibitors, there may be mentioned, for example, the following:

Nitro compounds other than halogenated nitro compounds, e.g. nitromethane, nitroethane, nitropropane, nitrobenzene, etc.;

Aromatic hydrocarbons, e.g. styrene, methylstyrene (α-, β-, o-, m-, p-), p-isopropenyltoluene, p-diisopropenylbenzene, p-isopropenylxylene, divinylbenzene (m-, p-), 1,1-diphenylethylene, etc.;

Unsaturated alicyclic hydrocarbons, e.g. cyclohexadiene, cyclopentadiene, α-pinene, α-limonene, furan, etc.;

Unsaturated aliphatic hydrocarbons, e.g. isoprene, 2-methyl-2-butene, 2,3-dimethylbutadiene, 2,3-dimethyl-1-butene, 1,3-pentadiene, 1-hexene, myrcene, etc.;

Epoxy compounds, e.g. 1,2-butylene oxide, isobutylene oxide, propylene oxide, epichlorohydrin, styrene oxide, glycidol, etc.;

Ether compounds, e.g. 1,4-dioxane, 1,2-dimethoxyethane, phenyl glycidyl ether, allyl glycidyl ether, furan, 2,5-dihydrofuran, furil, acetylacetone, etc.;

Phenol compounds, e.g. phenol, cresol (o-, m-, p-), methoxyphenol (o-, m-, p-), thymol, 2,6-di-tertbutyl-p-cresol, p-tert-butylphenol, eugenol, isoeugenol, anisole, isosafrole, p-tert-butylcatechol, etc.;

Unsaturated alcohols, e.g. propargyl alcohol, 3-methyl-1-buten-3-ol, 2-methyl-3-butyn-3-ol, etc.

The procedure for incorporating the decomposition inhibitor into compounds for polyurethane foam manufacture can suitably be selected. For instance, where a polyol and an organic isocyanate, which are principal components in compounds for polyurethane manufacture, are mixed and allowed to react with each other in the step of polyurethane foam formation, other additional components such as a blowing agent and are admixed with the polyol or organic isocyanate in advance. Therefore, it is possible to dissolve the decomposition inhibitor dissolved beforehand in the blowing agent and thus premix the inhibitor, together with the blowing agent, with the polyol or organic isocyanate, or to premix the decomposition inhibitor alone with the polyol or organic isocyanate. The means for mixing in each step can thus be selected arbitrarily.

As examples of the HCFCs/HFCs that can be stabilized in accordance with the present invention, there may be mentioned the following:

Hydrogen-containing chlorofluorohydrocarbons (HCFCs), e.g. monochlorodifluoromethane (HCFC 22; hereinafter the number alone is mentioned, as "22"), dichlorotrifluoroethane (123), monochlorotetrafluoroethane (124), dichloromonofluoroethane (141) and monochlorodifluoroethane (142);

Hydrogen-containing fluorohydrocarbons (HFCs), e.g. difluoromethane (32), difluoroethane (152), trifluoroethane (143), tetrafluoroethene (134), heptafluoropropane (227), hexafluoropropane (236), pentafluoropropane (245), hexafluorobutane (356) and octafluorobutane (338).

Where isomerism is possible for the HCFCs/HFCs mentioned above, the respective isomers may be used either singly or in the form of a mixture. It is to be noted that all such cases fall within the scope of the present invention.

It is further to be noted that not only the single use of such HCFCs/HFCs as blowing agents but also the combined use thereof with other blowing agents or water falls within the scope of the present invention as well.

As said other blowing agents that can be used in combination with HCFCs/HFCs in the decomposition inhibiting method of the invention, there may be mentioned, for example:

Low-boiling halogenated hydrocarbons, trichloromonofluoromethane, dichlorodifluoromethane, methylene chloride, perfluoropentane, etc.;

Low-boiling hydrocarbons, e.g. n-pentane, isopentane, cyclopentane, n-butane, isobutane, etc.;

Inert gases, e.g. air, nitrogen, carbon dioxide, etc.

As other raw materials to be used in manufacturing foamed insulation materials (polyurethane foams) by applying the present invention, there may be mentioned those well known in the art. Thus, the organic isocyanate, polyol, catalyst, foam controlling agent and other additives that are required for polyurethane foam formation may be as follows.

The organic isocyanate may include those aliphatic, alicyclic or aromatic isocyanates that are described in the monograph "Keiji Iwata: Polyurethane Resin Handbook, pages 71–98, published by Nikkan Kogyo Shinbunsha", for instance.

2,4-Tolylene diisocyanate (2,4-TDI), 2,6-tolylene diisocyanate (2,6-TDI) and mixtures of these (2,4-TDI/2,6-TDI ratio=80/20 or 65/35, for instance) are polyisocyanates most generally used. Another typical example is polyphenylpolymethylene polyisocyanate (crude MDI) produced by reacting an aniline-formaldehyde condensate with phosgene.

The polyol includes polyether polyols and polyester polyols (Keiji Iwata: Polyurethane Resin Handbook, pages 99–117, published by Nikkan Kogyo Shinbunsha).

The polyether polyols can be produced by reacting an active hydrogen-containing initiator with an alkylene oxide. In the practice of the present invention, polyether polyols having 2 to 8 functional groups and a hydroxyl value of 300 to 600 mg KOH/g as produced by reacting such an initiator compound as ethylene glycol, trimethylolpropane, glycerol, triethanolamine, ethylenediamine, methyl glucoside, tolylenediamine, sorbitol and/or sucrose with such an alkylene oxide as ethylene oxide and/or propylene oxide can be used.

The polyester polyols that can be used have 2 to 4 functional groups and a hydroxyl value of 250 to 500 mg KOH/g, including condensate polyester polyols produced by dehydration condensation of adipic acid and a glycol or triol, lactone polyesters produced by ring opening polymerization of caprolactone, and polycarbonate diols.

Usable as the catalyst are tertiary amines, organometallic compounds, and mixtures of these. The catalyst is generally used in an amount of 0.01 to 10%, preferably about 0.1 to 5%, relative to the foam-forming mixture (organic isocyanate+polyol+blowing agent).

As the tertiary amine, there may be mentioned monoamine such as triethylamine and dimethylcyclohexylamine, diamine such as tetramethylethylenediamine and tetramethylhexamethylenediamine, cyclic amines such as triethylenediamine and 1,2-dimethylimidazole, and alcohol amines such as dimethylaminoethanol, among others.

As the organometallic compounds, there may be mentioned stannous octoate, dibutyl tin dilaurate, dibutyltin diacetate and lead octenoate.

The foam controlling agent includes silicone surfactant and fluorine-containing surfactant, typically polysiloxane-polyalkylene block copolymers, methylpolysiloxane-based surfactant, etc.

One or more of known additives such as fillers, colorants, fire retardants, antifungal agents and mold release agent may be incorporated where appropriate.

Foamed insulation materials (polyurethane foams) can be produced by applying the present invention using the per se known methods of producing polyurethane foams without any particular modification. Thus, for instance, the method comprising reacting an organic polyisocyanate with an active hydrogen-containing compound, such as a polyol having at least two active-hydrogen-containing groups, in the presence of a catalyst and a blowing agent is well known for the production of polyurethane foams, and the established known processes include the one-shot process, prepolymer process and so forth. The present invention is effective in any of the methods and processes.

EFFECTS OF THE INVENTION

The decomposition inhibitors of the invention are excellent in the effect of inhibiting the decomposition of HCFCs/HFCs and, therefore, when foamed insulation materials (polyurethane foams) are produced using HCFCs/HFCs as blowing agents, said inhibitors can inhibit to a remarkable extent the decomposition of HCFCs/HFCs in any stage and in any state, namely not only during the raw material storage period preceding foam manufacture but also during the manufacture of foamed insulation materials (during the use of HCFCs/HFCs as blowing agents ) and the use of foamed insulation materials (polyurethane foam products). The decomposition inhibiting method of the invention is very useful from the practical viewpoint as a method of inhibiting the decomposition of HCFCs/HFCs in particular when the HCFCs/HCFs are used as blowing agents in the manufacture of foamed insulation materials.

EXAMPLES

The following examples and comparative examples illustrate the invention in further detail.

Examples 1 to 24 and Comparative Example 1

The materials used in the examples and comparative example were as follows:

Polyol: o-Tolylenediamine-based polyether polyol with a hydroxyl value of 400 mg KOH/g;

Foam controlling agent: Toray Silicone's silicone type foam controlling agent (trademark: "SH-193");

Catalyst: Tetramethylhexamethylenediamine;

Blowing agent: 1,1-Dichloro-1-fluoroethane (HCFC141b);

Decomposition inhibitors:

A: Nitrobenzene;

B: Monochloroacetic acid (1.9 g) +N-methylpyrrole (1.6 g)

C: Monochloroacetic acid (1.9 g) +N,N-dimethylaniline (2.4 g);

D: Monochloroacetic acid (1.9 g) +1,2-dimethylimidazole (1.9 g):

E: 1,1,1,2-Tetrachloroethane;

F: 2-Chloro-2-methylpropane;

G: 1-Chloropropane;

H: Methyl chloroacetate;

I: Ethyl chloroacetate;

J: Methyl bromoacetate;

K: Ethyl bromoacetate;

L: Chloroacetonitrile;

M: Bromoacetonitrile.

Organic isocyanate:
Polyphenylpolymethylenepolyisocyanate (crude MDI).

A mixture for rigid polyurethane foam manufacture was prepared by mixing up the polyol (100 parts), foam controlling agent (1.5 parts), catalyst (3.4 parts) and blowing agent (30 parts), together with the decomposition inhibitor specified in Table 1 (in the proportion indicated).

TABLE 1

| | STABILIZER | | | |
|---|---|---|---|---|
| | COMPOSITION | PROPORTION <PART(S)> | COMPOSITION | PROPORTION <PART(S)> |
| COMPARATIVE EXAMPLE 1 | A | 0.3 | | |
| EXAMPLE 1 | A | 0.3 | B | 3.5 |
| EXAMPLE 2 | A | 0.3 | C | 4.3 |
| EXAMPLE 3 | A | 0.3 | D | 3.8 |
| EXAMPLE 4 | A | 0.3 | E | 7.5 |
| EXAMPLE 5 | A | 0.3 | F | 7.5 |
| EXAMPLE 6 | A | 0.3 | G | 7.5 |
| EXAMPLE 7 | A | 0.3 | H | 1.5 |
| EXAMPLE 8 | A | 0.3 | I | 1.5 |
| EXAMPLE 9 | A | 0.3 | J | 1.5 |
| EXAMPLE 10 | A | 0.3 | K | 1.5 |
| EXAMPLE 11 | A | 0.3 | L | 1.5 |
| EXAMPLE 12 | A | 0.3 | M | 1.3 |
| EXAMPLE 13 | | | B | 3.5 |
| EXAMPLE 14 | | | C | 4.3 |
| EXAMPLE 15 | | | D | 3.8 |
| EXAMPLE 16 | | | E | 7.5 |
| EXAMPLE 17 | | | F | 7.5 |
| EXAMPLE 18 | | | G | 7.5 |
| EXAMPLE 19 | | | H | 1.5 |
| EXAMPLE 20 | | | I | 1.5 |

TABLE 1-continued

| | STABILIZER | | | |
|---|---|---|---|---|
| | COMPOSITION | PROPORTION <PART(S)> | COMPOSITION | PROPORTION <PART(S)> |
| EXAMPLE 21 | | | J | 1.5 |
| EXAMPLE 22 | | | K | 1.5 |
| EXAMPLE 23 | | | L | 1.5 |
| EXAMPLE 24 | | | M | 1.5 |

The organic isocyanate (71 parts) was added to the above mixture (100 parts). The whole mixture was made up into a polyurethane foam by the hand mixing technique and, after 1 day of maturation, the polyurethane foam was cut to cubes, 10 cm in edge size. The cubic pieces were vacuum-packed in laminated aluminum packs and then crushed using a press. The concentrations of decomposition gases <1-chloro-1-fluoroethylene (product A) and 1-chloro-1-fluoroethane (product B)> formed by the exothermic reaction were determined by gas chromatography for assessing the performance of the decomposition inhibitor in terms of the ability to inhibit the decomposition of the HCFC in the step of foam formation (during the reaction). The results obtained are shown in Table 2.

Furthermore, the same vacuum-packed polyurethane foam pieces as those mentioned above were maintained at 90° C. in a constant-temperature vessel for 2 weeks and the decomposition gas concentrations were then determined by gas chromatography to thereby assess the performance of the decomposition inhibitor in terms of the ability to inhibit the decomposition of the HCFC during aging. The results obtained are shown in Table 2.

TABLE 2

| | DECOMPOSITION GAS CONCENTRATION (ppm) | | | |
|---|---|---|---|---|
| | DURING THE REACTION | | DURING AGING | |
| | PRODUCT A | PRODUCT B | PRODUCT A | PRODUCT B |
| COMPATIVE EXAMPLE 1 | 100 | 20 | 10000 | 250 |
| EXAMPLE 1 | 0 | 0 | 10 | 0 |
| EXAMPLE 2 | 0 | 0 | 10 | 0 |
| EXAMPLE 3 | 0 | 0 | 10 | 0 |
| EXAMPLE 4 | 5 | 0 | 170 | 0 |
| EXAMPLE 5 | 10 | 0 | 290 | 0 |
| EXAMPLE 6 | 5 | 0 | 580 | 0 |
| EXAMPLE 7 | 0 | 0 | 10 | 0 |
| EXAMPLE 8 | 0 | 0 | 20 | 0 |
| EXAMPLE 9 | 0 | 0 | 10 | 0 |
| EXAMPLE 10 | 0 | 0 | 20 | 0 |
| EXAMPLE 11 | 0 | 0 | 0 | 0 |
| EXAMPLE 12 | 0 | 0 | 0 | 0 |
| EXAMPLE 13 | 0 | 0 | 10 | 5 |
| EXAMPLE 14 | 0 | 0 | 10 | 5 |
| EXAMPLE 15 | 0 | 0 | 10 | 5 |
| EXAMPLE 16 | 5 | 0 | 170 | 10 |
| EXAMPLE 17 | 10 | 0 | 290 | 10 |
| EXAMPLE 18 | 5 | 0 | 580 | 15 |
| EXAMPLE 19 | 0 | 0 | 10 | 5 |
| EXAMPLE 20 | 0 | 0 | 20 | 5 |
| EXAMPLE 21 | 0 | 0 | 10 | 5 |
| EXAMPLE 22 | 0 | 0 | 20 | 5 |
| EXAMPLE 23 | 0 | 0 | 10 | 10 |
| EXAMPLE 24 | 0 | 0 | 10 | 15 |

Examples 25 to 48 and Comparative Example 2

Polyurethane foams were produced in the same manner as in Examples 1 to 24 and Comparative Example 1 except that 1,1-dichloro-2,2,2-trifluoroethane (HCFC123) was used as the blowing agent. The stabilizers and proportions thereof used in the examples and comparative example are shown in Table 3.

The performance characteristics of each stabilizer as evaluated in the same manner as in Examples 1 to 24 and Comparative Example 1 and expressed in terms of the ability to inhibit the decomposition of the HCFC during reaction and during aging are shown in Table 4. The concentrations of 1,1-dichloro-2,2-difluoroethylene (product C) and 1-chloro-2,2,2-trifluoroethane (product D) were determined as the decomposition gas concentrations.

TABLE 3

| | STABILIZER | | | |
|---|---|---|---|---|
| | COMPOSITION | PROPORTION <PART(S)> | COMPOSITION | PROPORTION <PART(S)> |
| COMPARATIVE EXAMPLE 2 | A | 0.3 | | |
| EXAMPLE 25 | A | 0.3 | B | 3.5 |
| EXAMPLE 26 | A | 0.3 | C | 4.3 |
| EXAMPLE 27 | A | 0.3 | D | 3.8 |
| EXAMPLE 28 | A | 0.3 | E | 7.5 |
| EXAMPLE 29 | A | 0.3 | F | 7.5 |
| EXAMPLE 30 | A | 0.3 | G | 7.5 |
| EXAMPLE 31 | A | 0.3 | H | 1.5 |
| EXAMPLE 32 | A | 0.3 | I | 1.5 |
| EXAMPLE 33 | A | 0.3 | J | 1.5 |
| EXAMPLE 34 | A | 0.3 | K | 1.5 |
| EXAMPLE 35 | A | 0.3 | L | 1.5 |
| EXAMPLE 36 | A | 0.3 | M | 1.3 |
| EXAMPLE 37 | | | B | 3.5 |
| EXAMPLE 38 | | | C | 4.3 |
| EXAMPLE 39 | | | D | 3.8 |
| EXAMPLE 40 | | | E | 7.5 |
| EXAMPLE 41 | | | F | 7.5 |
| EXAMPLE 42 | | | G | 7.5 |
| EXAMPLE 43 | | | H | 1.5 |
| EXAMPLE 44 | | | I | 1.5 |
| EXAMPLE 45 | | | J | 1.5 |
| EXAMPLE 46 | | | K | 1.5 |
| EXAMPLE 47 | | | L | 1.5 |
| EXAMPLE 48 | | | M | 1.5 |

TABLE 4

| | DECOMPOSITION GAS CONCENTRATION (ppm) | | | |
|---|---|---|---|---|
| | DURING THE REACTION | | DURING AGING | |
| | PRODUCT C | PRODUCT D | PRODUCT C | PRODUCT D |
| COMPATIVE | 50 | 960 | 100 | 4800 |
| EXAMPLE 25 | 0 | 0 | 0 | 30 |
| EXAMPLE 26 | 0 | 0 | 0 | 20 |
| EXAMPLE 27 | 0 | 0 | 0 | 30 |
| EXAMPLE 28 | 0 | 0 | 5 | 30 |
| EXAMPLE 29 | 0 | 0 | 10 | 40 |
| EXAMPLE 30 | 0 | 0 | 5 | 20 |
| EXAMPLE 31 | 0 | 0 | 0 | 50 |
| EXAMPLE 32 | 0 | 0 | 0 | 70 |
| EXAMPLE 33 | 0 | 0 | 0 | 60 |
| EXAMPLE 34 | 0 | 0 | 10 | 80 |
| EXAMPLE 35 | 0 | 20 | 0 | 130 |
| EXAMPLE 36 | 0 | 30 | 0 | 150 |
| EXAMPLE 37 | 0 | 10 | 0 | 50 |
| EXAMPLE 38 | 0 | 5 | 0 | 35 |
| EXAMPLE 39 | 0 | 10 | 0 | 50 |
| EXAMPLE 40 | 0 | 10 | 5 | 50 |
| EXAMPLE 41 | 0 | 15 | 10 | 65 |

TABLE 4-continued

| | DECOMPOSITION GAS CONCENTRATION (ppm) | | | |
|---|---|---|---|---|
| | DURING THE REACTION | | DURING AGING | |
| | PRODUCT C | PRODUCT D | PRODUCT C | PRODUCT D |
| EXAMPLE 42 | 0 | 10 | 5 | 40 |
| EXAMPLE 43 | 0 | 10 | 0 | 70 |
| EXAMPLE 44 | 0 | 5 | 0 | 85 |
| EXAMPLE 45 | 0 | 10 | 0 | 80 |
| EXAMPLE 46 | 0 | 10 | 10 | 100 |
| EXAMPLE 47 | 0 | 20 | 0 | 130 |
| EXAMPLE 48 | 0 | 30 | 0 | 150 |

Examples 49 to 62 77 and 78

Polyurethane foams were produced in the same manner as in Examples 1 to 24 and Comparative Example 1 except that the decomposition inhibitors specifically shown in Table 5 (with the proportions thereof) were used as the stabilizers. The symbols (N, O, P, Q, R, S, T and U) used in Table 5 to identify the decomposition inhibitors respectively correspondent the following compounds:

N: β-Chloropropionitrile;
O: 1-Chloroacetone;
P: 1-Bromoacetone;
Q: 1,1-Dichloroacetone;
R: Chloronitromethane;
S: Bromonitromethane;
T: β-Chloronitroethane;
U: Isopropyl chloroacetate.

The performance characteristics of each stabilizer as evaluated in the same manner as in Examples 1 to 24 and Comparative Example 1 and expressed in terms of the ability to inhibit the decomposition of the HCFC during reaction and during aging are shown in Table 6, together with the data for Comparative Example 1 mentioned hereinbefore.

TABLE 5

| | STABILIZER | | | |
|---|---|---|---|---|
| | COMPOSITION | PROPORTION <PART(S)> | COMPOSITION | PROPORTION <PART(S)> |
| COMPARATIVE EXAMPLE 1 | A | 0.3 | | |
| EXAMPLE 49 | A | 0.3 | N | 1.5 |
| EXAMPLE 50 | A | 0.3 | O | 1.5 |
| EXAMPLE 51 | A | 0.3 | P | 1.5 |
| EXAMPLE 52 | A | 0.3 | Q | 1.5 |
| EXAMPLE 53 | A | 0.3 | R | 1.5 |
| EXAMPLE 54 | A | 0.3 | S | 1.5 |
| EXAMPLE 55 | A | 0.3 | T | 1.5 |
| EXAMPLE 56 | | | N | 1.5 |
| EXAMPLE 57 | | | O | 1.5 |
| EXAMPLE 58 | | | P | 1.5 |
| EXAMPLE 59 | | | Q | 1.5 |
| EXAMPLE 60 | | | R | 1.5 |
| EXAMPLE 61 | | | S | 1.5 |
| EXAMPLE 62 | | | T | 1.5 |
| EXAMPLE 77 | A | 0.3 | U | 1.5 |
| EXAMPLE 78 | | | U | 1.5 |

TABLE 6

| | DECOMPOSITION GAS CONCENTRATION (ppm) | | | |
|---|---|---|---|---|
| | DURING THE REACTION | | DURING AGING | |
| | PRODUCT A | PRODUCT B | PRODUCT A | PRODUCT B |
| COMPARATIVE EXAMPLE 1 | 100 | 20 | 10000 | 250 |
| EXAMPLE 49 | 0 | 0 | 10 | 0 |
| EXAMPLE 50 | 0 | 0 | 30 | 0 |
| EXAMPLE 51 | 0 | 0 | 30 | 0 |
| EXAMPLE 52 | 0 | 0 | 25 | 0 |
| EXAMPLE 53 | 0 | 0 | 20 | 0 |
| EXAMPLE 54 | 0 | 0 | 20 | 0 |
| EXAMPLE 55 | 0 | 0 | 15 | 0 |
| EXAMPLE 56 | 0 | 0 | 10 | 5 |
| EXAMPLE 57 | 0 | 0 | 30 | 10 |
| EXAMPLE 58 | 0 | 0 | 30 | 15 |
| EXAMPLE 59 | 0 | 0 | 25 | 5 |
| EXAMPLE 60 | 0 | 0 | 20 | 10 |
| EXAMPLE 61 | 0 | 0 | 20 | 10 |
| EXAMPLE 62 | 0 | 0 | 15 | 5 |
| EXAMPLE 77 | 0 | 0 | 15 | 0 |
| EXAMPLE 78 | 0 | 0 | 20 | 15 |

Examples 63 to 76, 79 and 80

Polyurethane foams were produced in the same manner as in Examples 1 to 24 and Comparative Example 1 except that HCFC 123 was used as the blowing agent and the decomposition inhibitors specified, together with the proportions, in Table 7 were used as the stabilizers.

The performance characteristics of each stabilizer as evaluated in the same manner as in Examples 1 to 24 and Comparative Example 1 and expressed in terms of the ability to inhibit the decomposition of the HCFC during reaction and during aging are shown in Table 8, together with the data for Comparative Example 2 mentioned hereinabove. The concentrations of 1,1-dichloro-2,2-difluoroethylene (product C) and 1-chloro-2,2,2-trifluoroethane (product D) were determined as the decomposition gas concentrations.

TABLE 7

| | STABILIZER | | | |
|---|---|---|---|---|
| | COMPOSITION | PROPORTION <PART(S)> | COMPOSITION | PROPORTION <PART(S)> |
| COMPARATIVE EXAMPLE 2 | A | 0.3 | | |
| EXAMPLE 63 | A | 0.3 | N | 1.5 |
| EXAMPLE 64 | A | 0.3 | O | 1.5 |
| EXAMPLE 65 | A | 0.3 | P | 1.5 |
| EXAMPLE 66 | A | 0.3 | Q | 1.5 |
| EXAMPLE 67 | A | 0.3 | R | 1.5 |
| EXAMPLE 68 | A | 0.3 | S | 1.5 |
| EXAMPLE 69 | A | 0.3 | T | 1.5 |
| EXAMPLE 70 | | | N | 1.5 |
| EXAMPLE 71 | | | O | 1.5 |
| EXAMPLE 72 | | | P | 1.5 |
| EXAMPLE 73 | | | Q | 1.5 |
| EXAMPLE 74 | | | R | 1.5 |
| EXAMPLE 75 | | | S | 1.5 |
| EXAMPLE 76 | | | T | 1.5 |
| EXAMPLE 79 | A | 0.3 | U | 1.5 |
| EXAMPLE 80 | | | U | 1.5 |

TABLE 8

| | DECOMPOSITION GAS CONCENTRATION (ppm) | | | |
|---|---|---|---|---|
| | DURING THE REACTION | | DURING AGING | |
| | PRODUCT C | PRODUCT D | PRODUCT C | PRODUCT D |
| COMPARATIVE EXAMPLE 2 | 50 | 960 | 100 | 4800 |
| EXAMPLE 63 | 0 | 10 | 0 | 100 |
| EXAMPLE 64 | 0 | 20 | 0 | 120 |
| EXAMPLE 65 | 0 | 15 | 5 | 150 |
| EXAMPLE 66 | 0 | 15 | 0 | 170 |
| EXAMPLE 67 | 0 | 20 | 0 | 130 |
| EXAMPLE 68 | 0 | 20 | 5 | 120 |
| EXAMPLE 69 | 0 | 15 | 0 | 100 |
| EXAMPLE 70 | 0 | 15 | 0 | 105 |
| EXAMPLE 71 | 0 | 20 | 0 | 120 |
| EXAMPLE 72 | 0 | 20 | 5 | 160 |
| EXAMPLE 73 | 0 | 15 | 0 | 175 |
| EXAMPLE 74 | 0 | 20 | 0 | 140 |
| EXAMPLE 75 | 0 | 20 | 5 | 130 |
| EXAMPLE 76 | 0 | 15 | 0 | 120 |
| EXAMPLE 79 | 0 | 10 | 0 | 100 |
| EXAMPLE 80 | 0 | 10 | 0 | 150 |

Examples 81 to 120

Polyurethane foams were produced in the same manner as in Examples 1 to 24 and Comparative Example 1 except that 1,1,1,3,3-pentafluoropropane (HFC 245fa) was used as the blowing agent. The stabilizers and proportions thereof used in the respective examples and comparative example are shown in Table 9.

The performance characteristics of each stabilizer as evaluated in the same manner as in Examples 1 to 24 and Comparative Example 1 and expressed in terms of the ability to inhibit the decomposition of the HFC during reaction and during aging are shown in Table 10. The concentration of 1,3,3,3-tetrafluoropropene (product E) was determined as the decomposition gas concentration.

TABLE 9

| | STABILIZER | | | |
|---|---|---|---|---|
| | COMPOSITION | PROPORTION <PART(S)> | COMPOSITION | PROPORTION <PART(S)> |
| COMPARATIVE EXAMPLE 3 | A | 0.3 | | |
| EXAMPLE 81 | A | 0.3 | B | 3.5 |
| EXAMPLE 82 | A | 0.3 | C | 4.3 |
| EXAMPLE 83 | A | 0.3 | D | 3.8 |
| EXAMPLE 84 | A | 0.3 | E | 7.5 |
| EXAMPLE 85 | A | 0.3 | F | 7.5 |
| EXAMPLE 86 | A | 0.3 | G | 7.5 |
| EXAMPLE 87 | A | 0.3 | H | 1.5 |
| EXAMPLE 88 | A | 0.3 | I | 1.5 |
| EXAMPLE 89 | A | 0.3 | J | 1.5 |
| EXAMPLE 90 | A | 0.3 | K | 1.5 |
| EXAMPLE 91 | A | 0.3 | L | 1.5 |
| EXAMPLE 92 | A | 0.3 | M | 1.3 |
| EXAMPLE 93 | A | 0.3 | N | 1.5 |
| EXAMPLE 94 | A | 0.3 | O | 1.5 |
| EXAMPLE 95 | A | 0.3 | P | 1.5 |
| EXAMPLE 96 | A | 0.3 | Q | 1.5 |
| EXAMPLE 97 | A | 0.3 | R | 1.5 |
| EXAMPLE 98 | A | 0.3 | S | 1.5 |
| EXAMPLE 99 | A | 0.3 | T | 1.5 |
| EXAMPLE 100 | A | 0.3 | U | 1.5 |
| EXAMPLE 101 | | | B | 3.5 |
| EXAMPLE 102 | | | C | 4.3 |
| EXAMPLE 103 | | | D | 3.8 |
| EXAMPLE 104 | | | E | 7.5 |
| EXAMPLE 105 | | | F | 7.5 |
| EXAMPLE 106 | | | G | 7.5 |
| EXAMPLE 107 | | | H | 1.5 |
| EXAMPLE 108 | | | I | 1.5 |
| EXAMPLE 109 | | | J | 1.5 |
| EXAMPLE 110 | | | K | 1.5 |
| EXAMPLE 111 | | | L | 1.5 |
| EXAMPLE 112 | | | M | 1.5 |
| EXAMPLE 113 | | | N | 1.5 |
| EXAMPLE 114 | | | O | 1.5 |
| EXAMPLE 115 | | | P | 1.5 |

TABLE 9-continued

| | STABILIZER | | | |
|---|---|---|---|---|
| | COMPOSITION | PROPORTION <PART(S)> | COMPOSITION | PROPORTION <PART(S)> |
| EXAMPLE 116 | | | Q | 1.5 |
| EXAMPLE 117 | | | R | 1.5 |
| EXAMPLE 118 | | | S | 1.5 |
| EXAMPLE 119 | | | T | 1.5 |
| EXAMPLE 120 | | | U | 1.5 |

TABLE 10

| | DECOMPOSITION GAS CONCENTRATION (ppm) | |
|---|---|---|
| | DURING THE REACTION PRODUCT E | DURING AGING PRODUCT E |
| COMPATIVE EXAMPLE 3 | 200 | 800 |
| EXAMPLE 81 | 0 | 5 |
| EXAMPLE 82 | 0 | 5 |
| EXAMPLE 83 | 0 | 5 |
| EXAMPLE 84 | 5 | 20 |
| EXAMPLE 85 | 5 | 25 |
| EXAMPLE 86 | 5 | 25 |
| EXAMPLE 87 | 0 | 5 |
| EXAMPLE 88 | 0 | 10 |
| EXAMPLE 89 | 0 | 5 |
| EXAMPLE 90 | 0 | 10 |
| EXAMPLE 91 | 0 | 5 |
| EXAMPLE 92 | 0 | 5 |
| EXAMPLE 93 | 0 | 10 |
| EXAMPLE 94 | 0 | 5 |
| EXAMPLE 95 | 0 | 10 |
| EXAMPLE 96 | 0 | 5 |
| EXAMPLE 97 | 0 | 5 |
| EXAMPLE 98 | 0 | 5 |
| EXAMPLE 99 | 0 | 5 |
| EXAMPLE 100 | 0 | 5 |
| EXAMPLE 101 | 0 | 10 |
| EXAMPLE 102 | 0 | 10 |
| EXAMPLE 103 | 0 | 10 |
| EXAMPLE 104 | 5 | 25 |
| EXAMPLE 105 | 10 | 35 |
| EXAMPLE 106 | 5 | 30 |
| EXAMPLE 107 | 0 | 10 |
| EXAMPLE 108 | 0 | 15 |
| EXAMPLE 109 | 0 | 10 |
| EXAMPLE 110 | 0 | 15 |
| EXAMPLE 111 | 0 | 10 |
| EXAMPLE 112 | 0 | 10 |
| EXAMPLE 113 | 0 | 15 |
| EXAMPLE 114 | 0 | 10 |
| EXAMPLE 115 | 0 | 15 |
| EXAMPLE 116 | 0 | 10 |
| EXAMPLE 117 | 0 | 10 |
| EXAMPLE 118 | 0 | 10 |
| EXAMPLE 119 | 0 | 10 |
| EXAMPLE 120 | 0 | 10 |

Examples 121 to 160

Polyurethane foams were produced in the same manner as in Examples 1 to 24 and Comparative Example 1 except that 1,1,2,2,3-pentafluoropropane (HFC 245ca) was used as the blowing agent. The stabilizers and proportions thereof used in the respective examples and comparative example are shown in Table 11.

The performance characteristics of each stabilizer as evaluated in the same manner as in Examples 1 to 24 and Comparative Example 1 and expressed in terms of the ability to inhibit the decomposition of the HFC during reaction and during aging are shown in Table 12. The concentration of 1,3,3,3-tetrafluoropropene (product F) was determined as the decomposition gas concentration.

TABLE 11

| | STABILIZER | | | |
|---|---|---|---|---|
| | COMPOSITION | PROPORTION <PART(S)> | COMPOSITION | PROPORTION <PART(S)> |
| COMPARATIVE EXAMPLE 4 | A | 0.3 | | |
| EXAMPLE 121 | A | 0.3 | B | 3.5 |
| EXAMPLE 122 | A | 0.3 | C | 4.3 |
| EXAMPLE 123 | A | 0.3 | D | 3.8 |
| EXAMPLE 124 | A | 0.3 | E | 7.5 |
| EXAMPLE 125 | A | 0.3 | F | 7.5 |
| EXAMPLE 126 | A | 0.3 | G | 7.5 |
| EXAMPLE 127 | A | 0.3 | H | 1.5 |
| EXAMPLE 128 | A | 0.3 | I | 1.5 |
| EXAMPLE 129 | A | 0.3 | J | 1.5 |
| EXAMPLE 130 | A | 0.3 | K | 1.5 |
| EXAMPLE 131 | A | 0.3 | L | 1.5 |
| EXAMPLE 132 | A | 0.3 | M | 1.3 |
| EXAMPLE 133 | A | 0.3 | N | 1.5 |
| EXAMPLE 134 | A | 0.3 | O | 1.5 |

TABLE 11-continued

| | STABILIZER | | | |
|---|---|---|---|---|
| | COMPOSITION | PROPORTION <PART(S)> | COMPOSITION | PROPORTION <PART(S)> |
| EXAMPLE 135 | A | 0.3 | P | 1.5 |
| EXAMPLE 136 | A | 0.3 | Q | 1.5 |
| EXAMPLE 137 | A | 0.3 | R | 1.5 |
| EXAMPLE 138 | A | 0.3 | S | 1.5 |
| EXAMPLE 139 | A | 0.3 | T | 1.5 |
| EXAMPLE 140 | A | 0.3 | U | 1.5 |
| EXAMPLE 141 | | | B | 3.5 |
| EXAMPLE 142 | | | C | 4.3 |
| EXAMPLE 143 | | | D | 3.8 |
| EXAMPLE 144 | | | E | 1.5 |
| EXAMPLE 145 | | | F | 7.5 |
| EXAMPLE 146 | | | G | 7.5 |
| EXAMPLE 147 | | | H | 1.5 |
| EXAMPLE 148 | | | I | 1.5 |
| EXAMPLE 149 | | | J | 1.5 |
| EXAMPLE 150 | | | K | 1.5 |
| EXAMPLE 151 | | | L | 1.5 |
| EXAMPLE 152 | | | M | 1.5 |
| EXAMPLE 153 | | | N | 1.5 |
| EXAMPLE 154 | | | O | 1.5 |
| EXAMPLE 155 | | | P | 1.5 |
| EXAMPLE 156 | | | Q | 1.5 |
| EXAMPLE 157 | | | R | 1.5 |
| EXAMPLE 158 | | | S | 1.5 |
| EXAMPLE 159 | | | T | 1.5 |
| EXAMPLE 160 | | | U | 1.5 |

TABLE 12

| | DECOMPOSITION GAS CONCENTRATION (ppm) | |
|---|---|---|
| | DURING THE REACTION PRODUCT F | DURING AGING PRODUCT F |
| COMPARATIVE EXAMPLE 4 | 30 | 200 |
| EXAMPLE 121 | 0 | 0 |
| EXAMPLE 122 | 0 | 0 |
| EXAMPLE 123 | 0 | 0 |
| EXAMPLE 124 | 0 | 10 |
| EXAMPLE 125 | 0 | 15 |
| EXAMPLE 126 | 0 | 15 |
| EXAMPLE 127 | 0 | 0 |
| EXAMPLE 128 | 0 | 5 |
| EXAMPLE 129 | 0 | 0 |
| EXAMPLE 130 | 0 | 5 |
| EXAMPLE 131 | 0 | 0 |
| EXAMPLE 132 | 0 | 0 |
| EXAMPLE 133 | 0 | 5 |
| EXAMPLE 134 | 0 | 0 |
| EXAMPLE 135 | 0 | 5 |
| EXAMPLE 136 | 0 | 0 |
| EXAMPLE 137 | 0 | 0 |
| EXAMPLE 138 | 0 | 0 |
| EXAMPLE 139 | 0 | 0 |
| EXAMPLE 140 | 0 | 0 |
| EXAMPLE 141 | 0 | 0 |
| EXAMPLE 142 | 0 | 0 |
| EXAMPLE 143 | 0 | 0 |
| EXAMPLE 144 | 5 | 10 |
| EXAMPLE 145 | 10 | 20 |
| EXAMPLE 146 | 5 | 15 |
| EXAMPLE 147 | 0 | 5 |
| EXAMPLE 148 | 0 | 10 |
| EXAMPLE 149 | 0 | 5 |
| EXAMPLE 150 | 0 | 10 |
| EXAMPLE 151 | 0 | 5 |
| EXAMPLE 152 | 0 | 5 |
| EXAMPLE 153 | 0 | 10 |
| EXAMPLE 154 | 0 | 5 |
| EXAMPLE 155 | 0 | 10 |
| EXAMPLE 156 | 0 | 5 |
| EXAMPLE 157 | 0 | 5 |
| EXAMPLE 158 | 0 | 5 |
| EXAMPLE 159 | 0 | 5 |
| EXAMPLE 160 | 0 | 5 |

Examples 161 to 200

Polyurethane foams were produced in the same manner as in Examples 1 to 24 and Comparative Example 1 except that 1,1,1,4,4,4-hexafluorobutane (HFC 365nff) was used as the blowing agent. The stabilizers and proportions thereof used in the respective examples and comparative example are shown in Table 13.

The performance characteristics of each stabilizer as evaluated in the same manner as in Examples 1 to 24 and Comparative Example 1 and expressed in terms of the ability to inhibit the decomposition of the HFC during reaction and during aging are shown in Table 14. The concentration of 1,1,4,4,4-pentafluorobutene (product G) was determined as the decomposition gas concentration.

TABLE 13

| | STABILIZER | | | |
|---|---|---|---|---|
| | COMPOSITION | PROPORTION <PART(S)> | COMPOSITION | PROPORTION <PART(S)> |
| COMPARATIVE EXAMPLE 5 | A | 0.3 | | |
| EXAMPLE 161 | A | 0.3 | B | 3.5 |
| EXAMPLE 162 | A | 0.3 | C | 4.3 |
| EXAMPLE 163 | A | 0.3 | D | 3.8 |
| EXAMPLE 164 | A | 0.3 | E | 7.5 |
| EXAMPLE 165 | A | 0.3 | F | 7.5 |
| EXAMPLE 166 | A | 0.3 | G | 7.5 |
| EXAMPLE 167 | A | 0.3 | H | 1.5 |
| EXAMPLE 168 | A | 0.3 | I | 1.5 |
| EXAMPLE 169 | A | 0.3 | J | 1.5 |
| EXAMPLE 160 | A | 0.3 | K | 1.5 |
| EXAMPLE 171 | A | 0.3 | L | 1.5 |
| EXAMPLE 172 | A | 0.3 | M | 1.5 |
| EXAMPLE 173 | A | 0.3 | N | 1.5 |
| EXAMPLE 174 | A | 0.3 | O | 1.5 |
| EXAMPLE 175 | A | 0.3 | P | 1.5 |
| EXAMPLE 176 | A | 0.3 | Q | 1.5 |
| EXAMPLE 177 | A | 0.3 | R | 1.5 |
| EXAMPLE 178 | A | 0.3 | S | 1.5 |
| EXAMPLE 179 | A | 0.3 | T | 1.5 |
| EXAMPLE 180 | A | 0.3 | U | 1.5 |
| EXAMPLE 181 | | | B | 3.5 |
| EXAMPLE 182 | | | C | 4.3 |
| EXAMPLE 183 | | | D | 3.8 |
| EXAMPLE 184 | | | E | 7.5 |
| EXAMPLE 185 | | | F | 7.5 |
| EXAMPLE 186 | | | G | 7.5 |
| EXAMPLE 187 | | | H | 1.5 |
| EXAMPLE 188 | | | I | 1.5 |
| EXAMPLE 189 | | | J | 1.5 |
| EXAMPLE 190 | | | K | 1.5 |
| EXAMPLE 191 | | | L | 1.5 |
| EXAMPLE 192 | | | M | 1.5 |
| EXAMPLE 193 | | | N | 1.5 |
| EXAMPLE 194 | | | O | 1.5 |
| EXAMPLE 195 | | | P | 1.5 |
| EXAMPLE 196 | | | Q | 1.5 |
| EXAMPLE 197 | | | R | 1.5 |
| EXAMPLE 198 | | | S | 1.5 |
| EXAMPLE 199 | | | T | 1.5 |
| EXAMPLE 200 | | | U | 1.5 |

TABLE 14

| | DECOMPOSITION GAS CONCENTRATION (ppm) | |
|---|---|---|
| | DURING THE REACTION PRODUCT G | DURING AGING PRODUCT G |
| COMPARATIVE EXAMPLE 5 | 150 | 900 |
| EXAMPLE 161 | 0 | 5 |
| EXAMPLE 162 | 0 | 5 |
| EXAMPLE 163 | 0 | 5 |
| EXAMPLE 164 | 5 | 20 |
| EXAMPLE 165 | 10 | 25 |
| EXAMPLE 166 | 5 | 25 |
| EXAMPLE 167 | 0 | 5 |
| EXAMPLE 168 | 5 | 15 |
| EXAMPLE 169 | 0 | 5 |
| EXAMPLE 170 | 0 | 10 |
| EXAMPLE 171 | 0 | 5 |
| EXAMPLE 172 | 0 | 5 |
| EXAMPLE 173 | 5 | 15 |
| EXAMPLE 174 | 0 | 5 |
| EXAMPLE 175 | 0 | 10 |
| EXAMPLE 176 | 0 | 5 |
| EXAMPLE 177 | 0 | 5 |
| EXAMPLE 178 | 0 | 5 |
| EXAMPLE 179 | 0 | 5 |
| EXAMPLE 180 | 0 | 5 |
| EXAMPLE 181 | 0 | 10 |
| EXAMPLE 182 | 0 | 10 |
| EXAMPLE 183 | 0 | 10 |
| EXAMPLE 184 | 5 | 25 |
| EXAMPLE 185 | 10 | 35 |
| EXAMPLE 186 | 10 | 30 |
| EXAMPLE 187 | 0 | 10 |
| EXAMPLE 188 | 10 | 15 |
| EXAMPLE 189 | 0 | 10 |
| EXAMPLE 190 | 5 | 15 |
| EXAMPLE 191 | 0 | 10 |
| EXAMPLE 192 | 0 | 15 |
| EXAMPLE 193 | 10 | 15 |
| EXAMPLE 194 | 0 | 10 |
| EXAMPLE 195 | 5 | 15 |
| EXAMPLE 196 | 0 | 10 |
| EXAMPLE 197 | 0 | 10 |
| EXAMPLE 198 | 0 | 10 |
| EXAMPLE 199 | 0 | 10 |
| EXAMPLE 200 | 0 | 10 |

Examples 201 to 240

Polyurethane foams were produced in the same manner as in Examples 1 to 24 and Comparative Example 1 except that 1,1,2,2,3,3,4,4-octafluorobutane (HFC 338pcc) was used as the blowing agent. The stabilizers and proportions thereof used in the respective examples and comparative example are shown in Table 15.

The performance characteristics of each stabilizer as evaluated in the same manner as in Examples 1 to 24 and Comparative Example 1 and expressed in terms of the ability to inhibit the decomposition of the HFC during reaction and during aging are shown in Table 16. The concentration of 1,1,2,3,3,4,4-heptafluoro-1-butene (product H) was determined as the decomposition gas concentration.

TABLE 15

| | STABILIZER | | | |
|---|---|---|---|---|
| | COMPOSITION | PROPORTION <PART(S)> | COMPOSITION | PROPORTION <PART(S)> |
| COMPARATIVE EXAMPLE 6 | A | 0.3 | | |
| EXAMPLE 201 | A | 0.3 | B | 3.5 |
| EXAMPLE 202 | A | 0.3 | C | 4.3 |
| EXAMPLE 203 | A | 0.3 | D | 3.8 |
| EXAMPLE 204 | A | 0.3 | E | 7.5 |
| EXAMPLE 205 | A | 0.3 | F | 7.5 |
| EXAMPLE 206 | A | 0.3 | G | 7.5 |
| EXAMPLE 207 | A | 0.3 | H | 1.5 |
| EXAMPLE 208 | A | 0.3 | I | 1.5 |
| EXAMPLE 209 | A | 0.3 | J | 1.5 |
| EXAMPLE 210 | A | 0.3 | K | 1.5 |
| EXAMPLE 211 | A | 0.3 | L | 1.5 |
| EXAMPLE 212 | A | 0.3 | M | 1.5 |
| EXAMPLE 213 | A | 0.3 | N | 1.5 |
| EXAMPLE 214 | A | 0.3 | O | 1.5 |
| EXAMPLE 215 | A | 0.3 | P | 1.5 |
| EXAMPLE 216 | A | 0.3 | Q | 1.5 |
| EXAMPLE 217 | A | 0.3 | R | 1.5 |
| EXAMPLE 218 | A | 0.3 | S | 1.5 |
| EXAMPLE 219 | A | 0.3 | T | 1.5 |
| EXAMPLE 220 | A | 0.3 | U | 1.5 |
| EXAMPLE 221 | | | B | 3.5 |
| EXAMPLE 222 | | | C | 4.3 |
| EXAMPLE 223 | | | D | 3.8 |
| EXAMPLE 224 | | | E | 7.5 |
| EXAMPLE 225 | | | F | 7.5 |
| EXAMPLE 226 | | | G | 7.5 |
| EXAMPLE 227 | | | H | 1.5 |
| EXAMPLE 228 | | | I | 1.5 |
| EXAMPLE 229 | | | J | 1.5 |
| EXAMPLE 230 | | | K | 1.5 |
| EXAMPLE 231 | | | L | 1.5 |
| EXAMPLE 232 | | | M | 1.5 |
| EXAMPLE 233 | | | N | 1.5 |
| EXAMPLE 234 | | | O | 1.5 |
| EXAMPLE 235 | | | P | 1.5 |
| EXAMPLE 236 | | | S | 1.5 |
| EXAMPLE 237 | | | R | 1.5 |
| EXAMPLE 238 | | | Q | 1.5 |
| EXAMPLE 239 | | | T | 1.5 |
| EXAMPLE 240 | | | U | 1.5 |

TABLE 16

| | DECOMPOSITION GAS CONCENTRATION (ppm) | |
|---|---|---|
| | DURING THE REACTION PRODUCT H | DURING AGING PRODUCT H |
| COMPARATIVE EXAMPLE 6 | 40 | 200 |
| EXAMPLE 201 | 0 | 0 |
| EXAMPLE 202 | 0 | 0 |
| EXAMPLE 203 | 0 | 0 |
| EXAMPLE 204 | 0 | 10 |
| EXAMPLE 205 | 0 | 15 |
| EXAMPLE 206 | 0 | 10 |
| EXAMPLE 207 | 0 | 0 |
| EXAMPLE 208 | 0 | 5 |
| EXAMPLE 209 | 0 | 0 |
| EXAMPLE 210 | 0 | 5 |
| EXAMPLE 211 | 0 | 0 |
| EXAMPLE 212 | 0 | 0 |
| EXAMPLE 213 | 0 | 5 |
| EXAMPLE 214 | 0 | 0 |
| EXAMPLE 215 | 0 | 5 |
| EXAMPLE 216 | 0 | 0 |
| EXAMPLE 217 | 0 | 0 |
| EXAMPLE 218 | 0 | 0 |
| EXAMPLE 219 | 0 | 0 |
| EXAMPLE 220 | 0 | 0 |
| EXAMPLE 221 | 0 | 0 |
| EXAMPLE 222 | 0 | 0 |
| EXAMPLE 223 | 0 | 0 |
| EXAMPLE 224 | 0 | 10 |
| EXAMPLE 225 | 5 | 20 |
| EXAMPLE 226 | 5 | 15 |
| EXAMPLE 227 | 0 | 0 |
| EXAMPLE 228 | 0 | 15 |
| EXAMPLE 229 | 0 | 0 |
| EXAMPLE 230 | 0 | 0 |
| EXAMPLE 231 | 0 | 0 |
| EXAMPLE 232 | 0 | 0 |
| EXAMPLE 233 | 0 | 0 |
| EXAMPLE 234 | 0 | 0 |
| EXAMPLE 235 | 0 | 0 |
| EXAMPLE 236 | 0 | 0 |
| EXAMPLE 237 | 0 | 0 |
| EXAMPLE 238 | 0 | 0 |
| EXAMPLE 239 | 0 | 0 |
| EXAMPLE 240 | 0 | 0 |

Examples 241 to 280

Polyurethane foams were produced in the same manner as in Examples 1 to 24 and Comparative Example 1 except that 1,1,1,2-tetrafluoroethane (HFC 134a) was used as the blowing agent. The stabilizers and proportions thereof used in the respective examples and comparative example are shown in Table 17.

The performance characteristics of each stabilizer as evaluated in the same manner as in Examples 1 to 24 and Comparative Example 1 and expressed in terms of the ability to inhibit the decomposition of the HFC during reaction and during aging are shown in Table 18. The concentration of 1,1,2-trifluoroethylene (product I) was determined as the decomposition gas concentration.

TABLE 17

| | STABILIZER | | | |
|---|---|---|---|---|
| | COMPOSITION | PROPORTION <PART(S)> | COMPOSITION | PROPORTION <PART(S)> |
| COMPARATIVE EXAMPLE 7 | A | 0.3 | | |
| EXAMPLE 241 | A | 0.3 | B | 3.5 |
| EXAMPLE 242 | A | 0.3 | C | 4.3 |
| EXAMPLE 243 | A | 0.3 | D | 3.8 |
| EXAMPLE 244 | A | 0.3 | E | 7.5 |
| EXAMPLE 245 | A | 0.3 | F | 7.5 |
| EXAMPLE 246 | A | 0.3 | G | 7.5 |
| EXAMPLE 247 | A | 0.3 | H | 1.5 |
| EXAMPLE 248 | A | 0.3 | I | 1.5 |
| EXAMPLE 249 | A | 0.3 | J | 1.5 |
| EXAMPLE 250 | A | 0.3 | K | 1.5 |
| EXAMPLE 251 | A | 0.3 | L | 1.5 |
| EXAMPLE 252 | A | 0.3 | M | 1.5 |
| EXAMPLE 253 | A | 0.3 | N | 1.5 |
| EXAMPLE 254 | A | 0.3 | O | 1.5 |
| EXAMPLE 255 | A | 0.3 | P | 1.5 |
| EXAMPLE 256 | A | 0.3 | Q | 1.5 |
| EXAMPLE 257 | A | 0.3 | R | 1.5 |
| EXAMPLE 258 | A | 0.3 | S | 1.5 |
| EXAMPLE 259 | A | 0.3 | T | 1.5 |
| EXAMPLE 260 | A | 0.3 | U | 1.5 |
| EXAMPLE 261 | | | B | 3.5 |
| EXAMPLE 262 | | | C | 4.3 |
| EXAMPLE 263 | | | D | 3.8 |
| EXAMPLE 264 | | | E | 7.5 |
| EXAMPLE 265 | | | F | 7.5 |
| EXAMPLE 266 | | | G | 7.5 |
| EXAMPLE 267 | | | H | 1.5 |
| EXAMPLE 268 | | | I | 1.5 |
| EXAMPLE 269 | | | J | 1.5 |
| EXAMPLE 270 | | | K | 1.5 |
| EXAMPLE 271 | | | L | 1.5 |
| EXAMPLE 272 | | | M | 1.5 |
| EXAMPLE 273 | | | N | 1.5 |
| EXAMPLE 274 | | | O | 1.5 |
| EXAMPLE 275 | | | P | 1.5 |
| EXAMPLE 276 | | | Q | 1.5 |
| EXAMPLE 277 | | | R | 1.5 |
| EXAMPLE 278 | | | S | 1.5 |
| EXAMPLE 279 | | | T | 1.5 |
| EXAMPLE 280 | | | U | 1.5 |

TABLE 18

| | DECOMPOSITION GAS CONCENTRATION (ppm) | |
|---|---|---|
| | DURING THE REACTION PRODUCT I | DURING AGING PRODUCT I |
| COMPATIVE EXAMPLE 7 | 40 | 250 |
| EXAMPLE 241 | 0 | 0 |
| EXAMPLE 242 | 0 | 0 |
| EXAMPLE 243 | 0 | 0 |
| EXAMPLE 244 | 0 | 10 |
| EXAMPLE 245 | 0 | 15 |
| EXAMPLE 246 | 0 | 15 |
| EXAMPLE 247 | 0 | 0 |
| EXAMPLE 248 | 0 | 5 |
| EXAMPLE 249 | 0 | 0 |
| EXAMPLE 250 | 0 | 5 |
| EXAMPLE 251 | 0 | 0 |
| EXAMPLE 252 | 0 | 0 |
| EXAMPLE 253 | 0 | 5 |
| EXAMPLE 254 | 0 | 0 |
| EXAMPLE 255 | 0 | 5 |
| EXAMPLE 256 | 0 | 0 |
| EXAMPLE 257 | 0 | 0 |
| EXAMPLE 258 | 0 | 0 |
| EXAMPLE 259 | 0 | 0 |
| EXAMPLE 260 | 0 | 0 |
| EXAMPLE 261 | 0 | 0 |
| EXAMPLE 262 | 0 | 0 |
| EXAMPLE 263 | 0 | 0 |
| EXAMPLE 264 | 5 | 10 |
| EXAMPLE 265 | 10 | 20 |
| EXAMPLE 266 | 5 | 15 |
| EXAMPLE 267 | 0 | 5 |
| EXAMPLE 268 | 0 | 10 |
| EXAMPLE 269 | 0 | 5 |
| EXAMPLE 270 | 0 | 10 |
| EXAMPLE 271 | 0 | 5 |
| EXAMPLE 272 | 0 | 5 |
| EXAMPLE 273 | 0 | 10 |
| EXAMPLE 274 | 0 | 5 |
| EXAMPLE 275 | 0 | 10 |
| EXAMPLE 276 | 0 | 5 |
| EXAMPLE 277 | 0 | 5 |
| EXAMPLE 278 | 0 | 5 |

TABLE 18-continued

| | DECOMPOSITION GAS CONCENTRATION (ppm) | |
|---|---|---|
| | DURING THE REACTION PRODUCT I | DURING AGING PRODUCT I |
| EXAMPLE 279 | 0 | 5 |
| EXAMPLE 280 | 0 | 5 |

We claim:

1. Stabilized compositions comprising a fluorine-containing hydrocarbon and a decomposition inhibitor which comprises at least one member of the class consisting of:
   (a) a mixture of at least one organic acid selected from the group consisting of monochloroacetic acid, dichloroacetic acid, trichloroacetic acid, trifluoroacetic acid, chlorobenzoic acid, aminobenzoic acid, nitrobenzoic acid, formic acid, citric acid, glutamic acid and oxalic acid and at least one amine selected from the group consisting of triethylenediamine, methylmorpholine, dimethylimidazole, dimethylaniline, methylpyrrole, pyridine, aminopyridine, methylpyridine and quinoline,
   (b) carboxylic acid ester selected from the group consisting of methyl chloroacetate, ethyl chloroacetate, isopropyl chloroacetate, methyl bromoacetate and ethyl bromoacetate,
   (c) nitrile compound selected from the group consisting of monochloroacetonitrile, dichloroacetonitrile, trichloroacetonitrile, α-chloropropionitrile, β-chloropropionitrile, monobromoacetonitrile, α-bromopropionitrile and β-bromopropionitrile,
   (d) carbonyl compound selected from the group consisting of 1-chloroacetone, 1,3-dichloroacetone, 1,1-dichloroacetone, 1-bromoacetone, 1,3-dibromoacetone and 1,1-dibromoacetone, and
   (e) halogenated nitro compound selected from the group consisting of monochloronitromethane, α-chloronitroethane, β-chloronitroethane, monobromonitromethane, α-bromonitroethane and β-bromonitroethane.

2. The stabilized compositions as defined in claim 1 which further comprises an aliphatic or aromatic nitro compound.

3. The stabilized compositions as defined in claim 2 which comprises at least one aliphatic or aromatic nitro compound selected from the group consisting of nitromethane, nitroethane, nitropropane and nitrobenzene.

4. The stabilized compositions as defined in one of claims 1, 2 or 3 wherein the fluorine-containing hydrocarbon is 1,1-dichloro-2,2,2-trifluoroethane, 1,1-dichloro-1-fluoroethane, 1,1,1,3,3-pentafluoropropane, 1,1,2,2,3-pentafluoropropane, 1,1,1,4,4,4-hexafluorobutane, 1,1,2,2,3, 3,4,4-octafluorobutane or 1,1,1,2-tetrafluoroethane.

5. A method of inhibiting the decomposition of hydrogen- and fluorine-containing halogenated hydrocarbons which comprises adding the decomposition inhibitor to fluorine-containing hydrocarbons, said decomposition inhibitor comprises at least one member of the class consisting of:
   (a) a mixture of at least one organic acid selected from the group consisting of monochloroacetic acid, dichloroacetic acid, trichloroacetic acid, trifluoroacetic acid, chlorobenzoic acid, aminobenzoic acid, nitrobenzoic acid, formic acid, citric acid, glutamic acid and oxalic acid and at least one amine selected from the group consisting of triethylenediamine, methylmorpholine, dimethylimidazole, dimethylaniline, methylpyrrole, pyridine, aminopyridine, methylpyridine and quinoline,
   (b) carboxylic acid ester selected from the group consisting of methyl chloroacetate, ethyl chloroacetate, isopropyl chloroacetate, methyl bromoacetate and ethyl bromoacetate,
   (c) nitrile compound selected from the group consisting of monochloroacetonitrile, dichloroacetonitrile, trichloroacetonitrile, α-chloropropionitrile, β-chloropropionitrile, monobromoacetonitrile, α-bromopropionitrile and β-bromopropionitrile,
   (d) carbonyl compound selected from the group consisting of 1-chloroacetone, 1,3-dichloroacetone, 1,1-dichloroacetone, 1-bromoacetone, 1,3-dibromoacetone and 1,1-dibromoacetone, and
   (e) halogenated nitro compound selected from the group consisting of monochloronitromethane, α-chloronitroethane, β-chloronitroethane, monobromonitromethane, α-bromonitroethane and β-bromonitroethane.

6. A method of inhibiting the decomposition of fluorine-containing hydrocarbons as defined in claim 5, wherein the fluorine-containing hydrocarbon is selected from the group consisting of 1,1-dichloro-2,2,2-trifluoroethane, 1,1-dichloro-1-fluoroethane, 1,1,1,3,3-pentafluoropropane, 1,1,2,2,3-pentafluoropropane, 1,1,1,4,4,4-hexafluorobutane, 1,1,2,2,3,3,4,4-octafluorobutane and 1,1,1,2-tetrafluoroethane.

* * * * *